(12) United States Patent
Kusters (10) Patent No.: US 12,385,769 B2
(45) Date of Patent: Aug. 12, 2025

(54) OPTICAL DEVICE AND METHOD FOR MEASURING FLOW RATE

(71) Applicant: Fenwal, Inc., Lake Zurich, IL (US)

(72) Inventor: Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 227 days.

(21) Appl. No.: 17/851,452

(22) Filed: Jun. 28, 2022

(65) Prior Publication Data

US 2023/0003564 A1 Jan. 5, 2023

Related U.S. Application Data

(60) Provisional application No. 63/217,588, filed on Jul. 1, 2021.

(51) Int. Cl.

| | | |
|---|---|---|
| *G01F 1/661* | (2022.01) | |
| *G01F 1/00* | (2022.01) | |
| *G01F 1/66* | (2022.01) | |
| *G01F 1/704* | (2006.01) | |
| *A61M 1/36* | (2006.01) | |

(52) U.S. Cl.
CPC .............. *G01F 1/661* (2013.01); *G01F 1/00* (2013.01); *G01F 1/662* (2013.01); *G01F 1/704* (2013.01); *A61M 1/3693* (2013.01)

(58) Field of Classification Search
CPC . G01F 1/661; G01F 1/662; G01F 1/74; G01F 23/2928; A61M 1/3693; A61M 1/3496; A61M 2202/0429; A61M 1/36224; A61M 1/36226; A61M 1/3622;

(Continued)

(56) References Cited

U.S. PATENT DOCUMENTS

| | | |
|---|---|---|
| 5,598,841 A | 2/1997 | Taniji et al. |
| 9,164,078 B2 | 10/2015 | Min et al. |
| (Continued) | | |

FOREIGN PATENT DOCUMENTS

| | | | |
|---|---|---|---|
| CA | 2583908 | * | 8/2013 |
| CN | 100566770 | * | 12/2009 |
| (Continued) | | | |

OTHER PUBLICATIONS

Extended European Search Report of Nov. 7, 2022 for European Application No. 22181411.4.

*Primary Examiner* — Robert R Raevis
(74) *Attorney, Agent, or Firm* — Cook Alex Ltd.

(57) ABSTRACT

An optical sensor device configured for use in combination with a fluid flowing through a tubing, the optical sensor device includes a light source configured to emit a light, with at least a portion of the light being exposed to a fluid in the tubing and reflected, an optical sensor configured to receive at least a portion of the reflected light and analyze at least a portion of the received reflected light to determine a reflectance measurement, and a controller configured to correlate the reflectance measurement to an input particulate level and generate an output indicative of the fluid flow rate corresponding to the reflectance measurement. Also disclosed is a method of optically measuring fluid flow rate in a fluid processing system including optically monitoring fluid flow through a transparent portion of a tubing by measuring light reflectance of particles in the fluid.

20 Claims, 6 Drawing Sheets

(58) Field of Classification Search
CPC ........ A61M 1/3663; A61M 2205/3306; A61M 2205/3334; A61M 1/1647
USPC ...... 73/1.16, 1.34, 23.33, 28.01, 61.71, 861, 73/861.41; 356/39–42, 337–343, 441, 356/442; 250/356.1, 559.32; 600/504
See application file for complete search history.

(56) References Cited

U.S. PATENT DOCUMENTS

| | | |
|---|---|---|
| 10,893,829 B2 | 1/2021 | Kusters et al. |
| 2012/0002189 A1 | 1/2012 | Bengoechea Apezteguia et al. |
| 2012/0004865 A1 | 1/2012 | Porro et al. |

FOREIGN PATENT DOCUMENTS

| | | | | |
|---|---|---|---|---|
| CN | 109924969 | * | 6/2019 | |
| CN | 112638442 A | * | 4/2021 | .......... A61M 1/1601 |
| DE | 112016000229 T5 | * | 9/2017 | .............. A61M 5/14 |
| EA | 114659952 | * | 6/2022 | |
| EP | 2837237 | * | 2/2015 | |
| JP | 2015181800 A | | 10/2015 | |
| JP | 2017009535 A | * | 1/2017 | .......... A61M 27/006 |
| WO | 2007105805 | * | 9/2007 | |
| WO | WO-2011113602 A1 | * | 9/2011 | ............ A61M 1/101 |

\* cited by examiner

OPTICAL DEVICE AND METHOD FOR MEASURING FLOW RATE

CROSS-REFERENCE TO RELATED APPLICATION

This application claims the benefit of U.S. Provisional Application No. 63/217,588, filed Jul. 1, 2021, which is hereby incorporated herein by reference.

BACKGROUND

Field of the Disclosure

The invention relates to devices and methods of measuring flow rates within fluid processing systems. More particularly, the invention relates to an optical device and method for measuring the flow rate of a fluid containing particles.

Description of Related Art

Many fluid processing systems involve moving fluid through one or more sections of conduit, pipe, or what generally will be referred to herein as tubing, regardless of the rigidity or material used to construct the tubing. Examples of fluid processing systems having fluids flowing through tubing include, for example, various blood processing systems that make it possible to collect particular blood constituents. For instance, whole blood typically is separated into its constituents (e.g., red cells, platelets, and plasma) through centrifugation, such as in the AMICUS® separator system from Fenwal, Inc., of Lake Zurich, Illinois, which is an affiliate of Fresenius Kabi A G of Bad Homburg, Germany, or other centrifugal apheresis separation devices, or a spinning membrane-type separators, such as the AUTOPHERESIS-C® and AURORA® devices from Fenwal, Inc.

One of the challenges with a fluid processing system is measuring fluid flow at different points within the system. This can be particularly difficult due to the type of fluids being processed. Current devices for blood processing tend to rely on pump stroke volume calculations and/or weight scale readings to estimate flow rates. At times, these techniques may have undesirable variability. Alternatively, ultrasound sensors may be considered for use, but the high cost of ultrasound flow measurement has been cost prohibitive, for example, when seeking to design cost-effective apheresis devices. Therefore, there is a need for a relatively low-cost, non-invasive sensor capable of measuring flow rates of fluids containing particles, such as for use in apheresis systems.

It should be noted that optical based sensors historically have been applied in apheresis systems to non-invasively monitor the particle or cellular content of fluid within a vessel or tubing, such as cell or free Hemoglobin (HGB) concentrations, using light transmission or reflection-based techniques. Examples of reflection sensing devices are described in U.S. Pat. Nos. 9,164,078 and 10,893,829, which are owned by the present Applicant and incorporated herein in their entireties.

It may be of significant benefit for fluid processing systems to employ optical sensors. However, it generally has been known that with apheresis systems transmission-based measurements are not effective for most cell concentrations handled by such systems. For instance, the cell content of whole blood (WB) or of packed red blood cells (RBCs) prevents measurable light from transmitting through the fluid. As such, it is generally believed that transmission-based optical sensors may not function well with fluids such as WB or RBCs. However, such sensors do work very well with platelet concentrate (PC) or platelet rich plasma (PRP).

SUMMARY

The present subject matter has a number of aspects which may be used in various combinations, in various fluid processing systems and the disclosure of one or more specific embodiments is for the purpose of disclosure and description, and not limitation. This summary highlights only a few of the aspects of this subject matter, and additional aspects are disclosed in the drawings and the more detailed description that follows.

In the present invention, light reflection measurements are utilized as the foundation of a device and method to measure the flow rate of a fluid containing cellular, or more generally, particle content. It may be possible to use non-invasive optical sensors to apply light transmission measurements with specific fluid types. The method requires the cell content to be high enough to detect changes in reflection and thus the method will be most effective with fluids such as WB and packed RBCs, and may not function well with fluid such as PC or PRP, although the method shall not be limited to red blood cell containing fluids. Red cell containing fluids have cell concentrations on the order of $10^6$/uL, whereas platelet containing fluids have cell concentrations on the order of $10^3$/uL. By way of the present application, a method is provided for measuring fluid flow using a light source and non-invasive optical sensor, for example, as part of a blood processing procedure.

Figure 1:
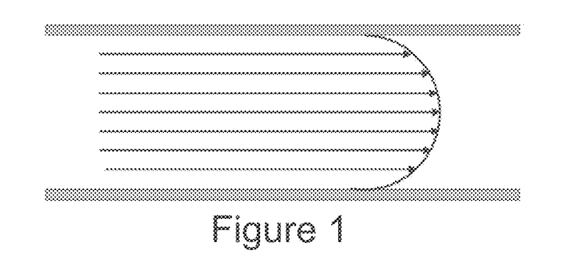
FIG. 1 is a diagram of a tubing cross-section representing a laminar flow velocity profile of fluid flowing through the tubing.
Figure 2:
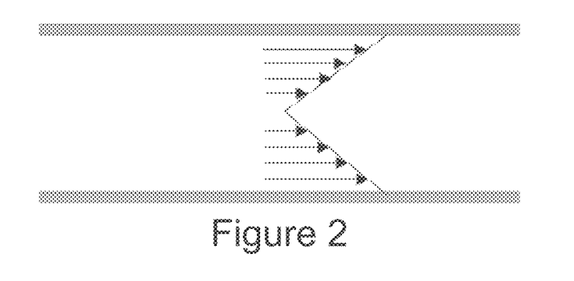
FIG. 2 is a diagram of the tubing cross-section of FIG. 1 representing the laminar flow shear stress forces that act on a particle in the fluid flow.

Importantly, the present device and method make use of certain properties of fluid flow. For instance, when fluid flows through a tubing, a laminar flow velocity profile is formed. This is shown, for example, in a diagram of a tubing cross-section shown in FIG. 1. Velocity streamlines of the laminar flow profile are useful in explaining the present invention. It will be appreciated that the shear stresses in the diagram shown in FIG. 2 represent the forces that act upon a particle during fluid flow in such a tubing. At the tubing walls, where shear stress is largest, a no-slip condition exists in which the fluid velocity is zero. Moving toward the center of the tubing, the velocity increases with a maximum velocity streamline in the center where the shear stress is nearly zero. When cells are present in the fluid, the streamlines will force the cells to the center of the tubing, where the velocity is greatest and the shear stress is lowest. Faster flow rates lead to a greater concentration of cells in the central streamlines.

Figure 3:
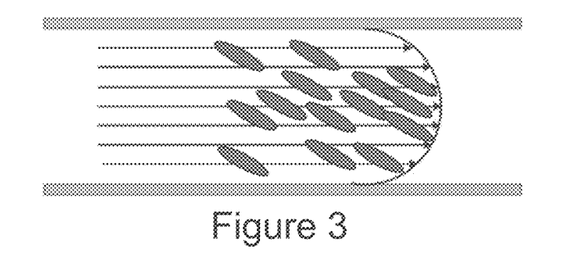
FIG. 3 is a diagram of the tubing cross-section of FIG. 1 representing a cell distribution profile at a relatively slower fluid flow rate.
Figure 4:
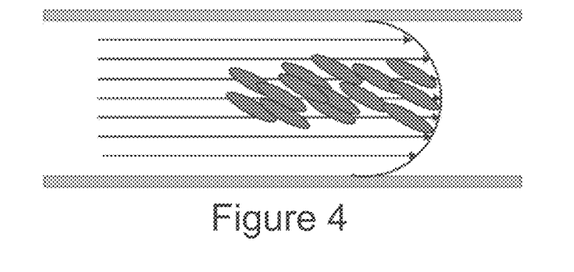
FIG. 4 is a diagram of the tubing cross-section of FIG. 1 representing a cell distribution profile at a relatively faster flow rate.

An example cell distribution profile in the fluid path is shown in the diagram of the tubing cross-section in FIG. 3 for a relatively slower fluid flow rate that congregates cells toward the center, but still contains some cells in the outer streamlines toward the tubing walls. The diagram of the tubing cross-section in FIG. 4 displays an example of a cell distribution profile in the fluid path for a relatively faster flow rate that congregates cells closer to the center of the tubing in comparison to the relatively slower flow rate of FIG. 3.

Figure 5:
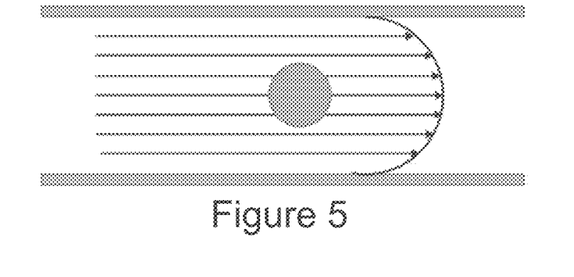
FIG. 5 is a diagram of the tubing cross-section of FIG. 1 representing the target or general location sought to be measured by a hypothetical reflection sensor, which is the center area of the tubing.

If a reflection sensor, containing a light source and detector on the same side of the tubing, were to be aimed at the center of the tubing, such as at the area represented in FIG. 5, it would become evident that at slower flow rates, when cells are more dispersed, there is more open fluid (non-particle containing fluid) permitting more light to transmit through the fluid in comparison to faster flow rates when cells would be more concentrated at the center of the tubing and within the viewing area of the sensor, causing more reflection of light. Therefore, for a fluid having particles such as cells, since the distribution of cells changes with respect to flow rate, and at a given flow rate the concentration of cells will tend to remain constant, the amount of light reflection measured by an optical sensor may be correlated to the flow rate of the fluid flowing through the tubing, so as to provide a measurement of the fluid flow.

In one aspect, a method of optically measuring a fluid flow rate in a fluid processing system is provided. The method includes optically monitoring fluid flow through a transparent portion of a tubing by measuring light reflectance of particles in the fluid, calculating the natural log relating to the reflectance of particles in the fluid, selecting two correlation curve coefficients based on a particulate value for the fluid which is input by a user, and calculating a fluid flow rate related to the two correlation curve coefficients and the natural log of the reflectance.

In another aspect, a method of measuring a flow rate of a fluid having particles is provided. The method includes providing a fluid flowing through a tubing, exposing the fluid in the tubing to a light emitted by a light source so as to cause at least a portion of the light to be reflected by the fluid, receiving at least a portion of the reflected light, analyzing at least a portion of the received light to determine a reflectance measurement of the at least a portion of the received light, correlating the reflectance measurement to a particulate value input by a user, and calculating a flow rate related to the reflectance measurement and the particulate value.

In yet another aspect, a device is provided for measuring fluid flow rate using optical measurements and configured for use in combination with a tubing in a fluid processing system. The device includes an optical sensor having a light source configured to emit a light, with at least a portion of the light being exposed to a fluid flowing through the tubing and being reflected. The optical sensor further includes an optical fiber for receiving at least a portion of the reflected light, and a controller configured to correlate the received reflected light relative to two correlation curve coefficients based on a particulate value input by a user and to calculate an output indicative of the flow rate of the fluid flowing through the tubing.

In another aspect, a method of measuring a flow rate of a fluid is provided. The method includes providing a fluid flowing through a tubing, exposing the fluid in the tubing to a light emitted by a light source so as to cause at least a portion of the light to be reflected by the fluid, receiving at least a portion of the reflected light, analyzing at least a portion of the received reflected light to determine a reflectance measurement, correlating the reflectance measurement to a particulate concentration, and generating an output indicative of the flow rate corresponding to the reflectance measurement.

In a further aspect, an optical sensor device is provided with the device configured for use in combination with a fluid flowing through a tubing. The optical sensor device includes a light source configured to emit a light, with at least a portion of the light being exposed to a fluid in the tubing and reflected. The device further includes an optical sensor configured to receive at least a portion of the reflected light and analyze at least a portion of the received reflected light to determine a reflectance measurement, and a controller configured to correlate the reflectance measurement to an input particulate level and generate an output indicative of the fluid flow rate corresponding to the reflectance measurement.

In yet another aspect, a method is provided for measuring the fluid flow rate of blood in a blood processing procedure. The blood processing procedure is a procedure in which blood is processed into one or more blood components with a single-use processing kit, the processing kit including tubing through which the blood is flowed, and a reusable hardware module onto which the processing kit is mounted, the reusable hardware module including a sensing field defined by a segment of the tubing to which a non-invasive optical reflection sensor is directed. The method includes loading the processing kit onto the hardware module with a segment of the tubing positioned in the sensing field, flowing blood through the segment of the tubing, accepting input of a hematocrit level of the blood flowing through the segment of the tubing positioned in the sensing field, utilizing the optical reflection sensor to apply light to the blood flowing through the tubing in the sensing field and obtain a reflectance measurement of the segment of the tubing through which said blood is flowing. The method further includes deriving the natural log of the infrared reflectance measurement attributable to the blood flowing in the segment of the tubing, selecting correlation curve coefficients based on the input hematocrit level, utilizing the natural log of the reflectance attributable to the blood in the segment of the tubing and the correlation curve coefficients in a correlation equation to arrive at the fluid flow rate measurement of the blood flowing through the tubing in the sensing field, and outputting the fluid flow rate measurement of the blood.

It will be appreciated that the use of an optical reflection sensor to measure flow rate of a fluid flowing through a tubing may be conducted with a cost efficient, non-invasive device using an advantageous method.

DETAILED DESCRIPTION

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

It will be appreciated that an optical reflection-based sensing design may be applicable to measure the amount of light reflection from a fluid flowing through a tubing. Such tubing may be included in a fluid processing device having a fixed fluid flow circuit. Alternatively, the tubing may be part of a disposable fluid flow circuit, which may be in a configuration of a module or cassette.

Figure 6:
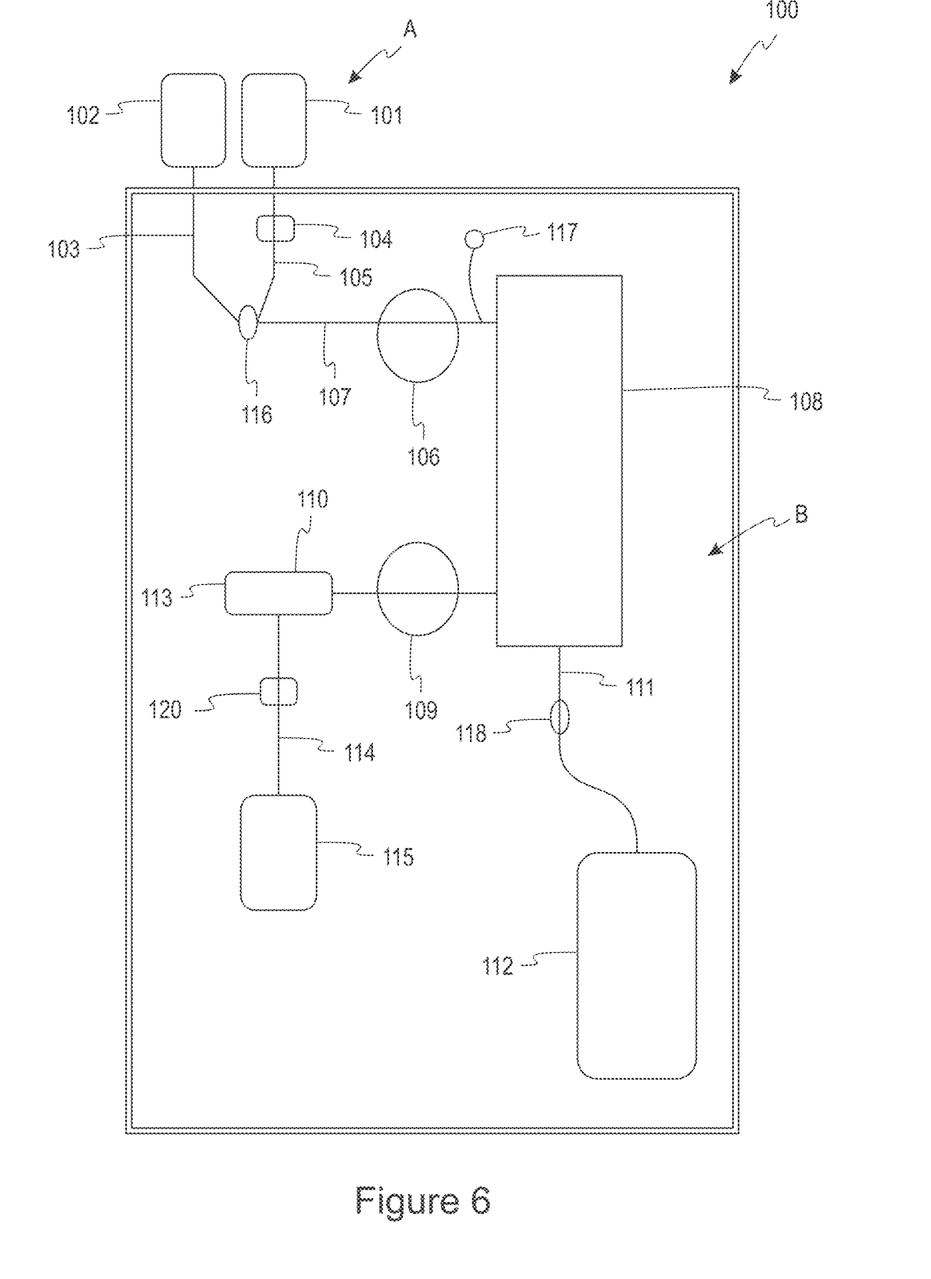
FIG. 6 is a schematic view of an automated fluid processing system, in the configuration of a blood separation system for processing blood including a disposable fluid flow circuit module and a durable controller or control module with the fluid flow circuit module assembled thereon.

Turning now to FIG. 6, a disposable fluid flow circuit or module A and a reusable durable controller or module B configured to cooperate with and control flow through the fluid circuit A are schematically illustrated as part of a fluid processing system 100. The disposable fluid circuit A as illustrated in FIG. 6 includes various components interconnected by flexible plastic tubing defining flow paths between the components. The fluid flow circuit or module A preferably is fully pre-assembled and pre-sterilized (with the possible exception of the unit of whole blood (WB) container and the cell preservative container). More specifically, the fluid processing system 100 is configured for processing blood, such as may be achieved with an apheresis fluid separation system. Thus, the illustrated disposable fluid circuit A in FIG. 6 is for the processing of previously collected WB. The circuit includes WB container 101, a cell preservation solution container 102, blood component separator 108, plasma collection container 112, optional leukocyte reduction filter 113, and red blook cell (RBC) collection container 115. While not illustrated in FIG. 6, the reusable module B may have hangers with associated weigh scales for supporting any or all of the containers 101, 102, 112 and 115.

The WB collection container 101 may be any suitable container but is typically a flexible plastic pouch or bag in which approximately 450 ml of whole blood have been previously collected. The container 101 may be either part of a separate system during collection and then joined to the rest of the fluid circuit A or actually part of the circuit A at the time of collection. At the time collection, in accordance with customary procedure, the WB is mixed with an anticoagulant located in the primary container to prevent premature coagulation. Accordingly, "whole blood" (WB) as used herein may include blood mixed with anticoagulant.

Flexible plastic tubing 105 is attached to the WB collection container, such as by a sterile connection device or other suitable attachment mechanism, and defines a WB fluid flow path between the WB container 101 and a junction with cell preservative solution tubing 103, which extends from the cell preservation solution container 102 to the flow path junction. The flow path junction between the WB flow path and all preservative flow path is located at inlet clamp 116. From the junction, the flow path extends through tubing 107 to an inlet port in the separator 108.

As shown in FIG. 6, the separator housing has an outlet that communicates with the gap between the housing and rotor and with concentrated red cell flow path tubing 110 for withdrawing concentrated red cells from the separator gap. In addition, the housing includes an outlet from the rotor that communicates with the side of the membrane facing away from the gap (for example, the interior of the rotor) and communicates with plasma flow path tubing 111.

For reducing the number of leukocytes that may be present in the red cells, the disposable fluid flow circuit A optionally includes a leukocyte reduction filter 113, which may be of any suitable well-known construction for removing leukocytes from concentrated red cells without unduly causing hemolysis of red cells or reducing the number of red cells in the collected product. The concentrated red cells flow from the leukocyte reduction filter 113 through a continuation tubing 114 of the concentrated red cell flow path into storage container 115 which may be of any suitable plastic material compatible with red cell storage.

Figures 7, 7A:
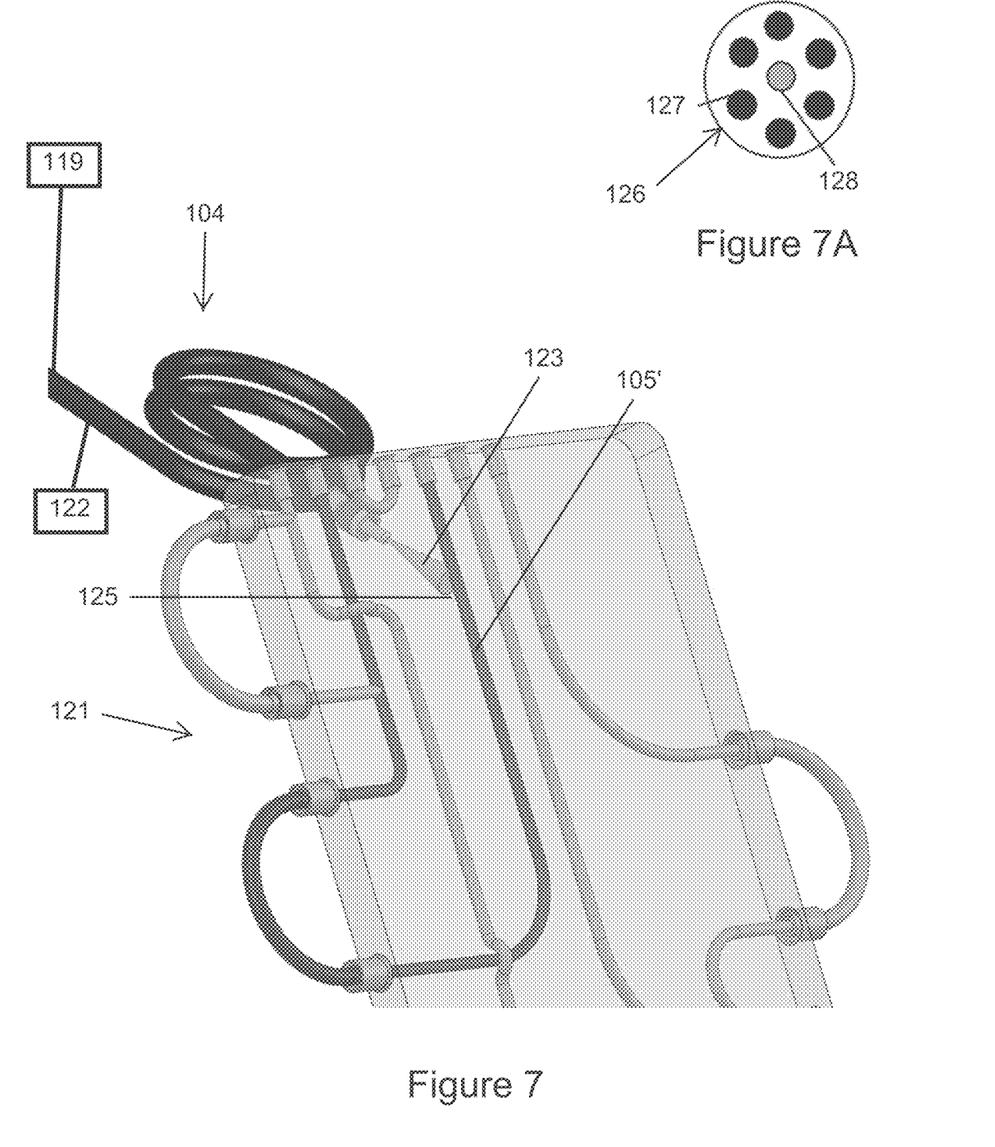
FIG. 7 is a perspective view of an example optical reflection sensor interacting with an example fluid tubing of a fluid processing system.
FIG. 7A is a diagram of a cross-section of the example optical reflection sensor of FIG. 6.

The reusable or durable controller module B, as shown in the FIG. 6 schematic, preferably includes a controller 119 (see FIG. 10) and an optical reflection sensor 104, as described more fully with respect to FIGS. 7 and 7A. The optical reflection sensor 104 measures the fluid flow of the WB flowing from the WB container 101. A particulate value for the fluid, which in this example is an HCT value for the WB, is input by the user into the controller 119. The HCT value to be input may be determined in advance, for example, by measuring a finger prick blood sample.

The durable reusable controller or control module B also includes an inlet clamp 116 which may be operated to control fluid from the WB container 101 or the cell preservative container 102 or, optionally, simultaneously and proportionally from both of the containers 101 and 102. For controlling flow of blood into the separator, the reusable module includes an inlet pump 106, which also may be of any suitable construction, and may be, for example, a peristaltic type pump which operates by progressive compression or squeezing of the tubing 107 forming the inlet flow path into the separator, a flexible diaphragm pump or other suitable pump. A pressure sensor 117 communicates with the inlet flow path between the pump 106 and the separator 108 to determine the inlet pumping pressure. The components interact with the controller 119 and the pressure sensor 117 may output to the controller 119 to provide an alarm function in the event of an over-pressure condition or an under-pressure condition or both.

To control the flow rate of concentrated RBCs from the separator 108, the reusable module B also includes an outlet pump 109 that is associated with the outlet flow path 110, and functions in the manner similar to that described with respect to inlet pump 106, as directed by the controller 119. It also may be of any suitable construction such as a peristaltic pump, a flexible diaphragm or other suitable pumping structure. The plasma flow path 111 exiting the separator is preferably not controlled by a pump, and the volumetric flow rate through the plasma flow path tubing is the difference between the inlet volumetric flow rate from pump 106 and the outlet volumetric flow rate from pump 109. Reusable module B may, however, also include a clamp 118 for controlling flow of plasma through the plasma flow path tubing 111. In addition to or as an alternative to the optical reflection sensor 104 measuring flow from the WB container 101, reusable module B also may include an optical reflection sensor clamp 120, similar to that of optical reflection sensor 104, for measuring the fluid flow from the outlet flow path 110 to the red cell collection container 115, in communication with the controller 119.

The disposable module A also may include a plasma collection container 112 in fluid communication with the plasma flow path for receiving plasma separated by the separator 108. Because the plasma passes through a porous membrane in the separator 108, the plasma that is collected in container 112 is largely cell free plasma and may be suitable for administration to patients, freezing for storage or subsequent processing.

FIG. 7 displays an example of the optical reflection sensor 104, applying a fiber-based design, shown for convenience in the context of an example alternative configuration with a portion of a fluid flow cassette 121. The optical reflection sensor 104 is in communication with the controller 119 and includes a light source 122. The light source 122 is configured to emit light 123 including which may be infrared, a single wavelength colored light or Broadband light having at least all wavelengths in the visible range (from approximately 400 nm to approximately 700 nm).

The light source 122 is oriented to emit light 123 toward a tubing 105', which is shown in a fluid flow circuit in the alternative form of example fluid flow cassette 121, but it will be appreciated that tubing 105' is representative of tubing 105 within the context of the disposable fluid flow circuit or module A of FIG. 6. As such, tubing 105' and 105 may be used interchangeably for explanation purposes within this disclosure. At least a portion of the side wall of the tubing 105' is transparent in the location where the optical reflection sensor 104 transmits the light 123 to measurer light reflectance of particles in the fluid, thereby monitoring fluid flow and permitting a determination of the fluid flow rate.

At least a portion of the light 123 is transmitted through a transparent surface 125 of the tubing 105' and into the tubing 105' to contact the fluid flowing therein, which is WB in example fluid processing system 100. It will be appreciated that the optical sensor 104 may be directed to have the light 123 strike the surface 125 of the tubing 105' at an angle, which may be selected to reduce the degree of specular reflection. The light source 122 itself may be oriented to direct the light 123 at a particular angle with respect to the surface 125 of the tubing 105'. Alternatively, at least one transmitting optical fiber may be provided to direct at least a portion of the light 123 from the light source 122 to the surface 125 of the tubing 105' at a particular angle.

FIG. 7A shows a cross-section of an optical fiber bundle 126, which includes a plurality of optical fibers. In one embodiment, the optical fiber bundle 126 is provided as a fiber bundle reflection probe of the type marketed by Thorlabs, Inc., having optical fibers with a 200 μm diameter. The cross-sectional view shows seven optical fibers, with six outer optical fibers 127 and one inner optical fiber 128 positioned centrally with respect to the outer optical fibers 127. In this example, the outer optical fibers 127 comprise transmitting optical fibers configured to transmit the 123 from the light source 122 to the surface 125 of the tubing 105', while the central or inner optical fiber 128 comprises a receiving optical fiber configured to transmit reflected light to the controller 119. It should be understood, however, that the illustrated configuration of the optical fiber bundle 126 is merely exemplary and that other configurations may also be employed if an optical fiber bundle is provided. For example, in other embodiments, there may be only a single transmitting optical fiber, a plurality of receiving optical fibers, and/or optical fibers differently arranged than as shown in FIG. 7A.

Figure 8:
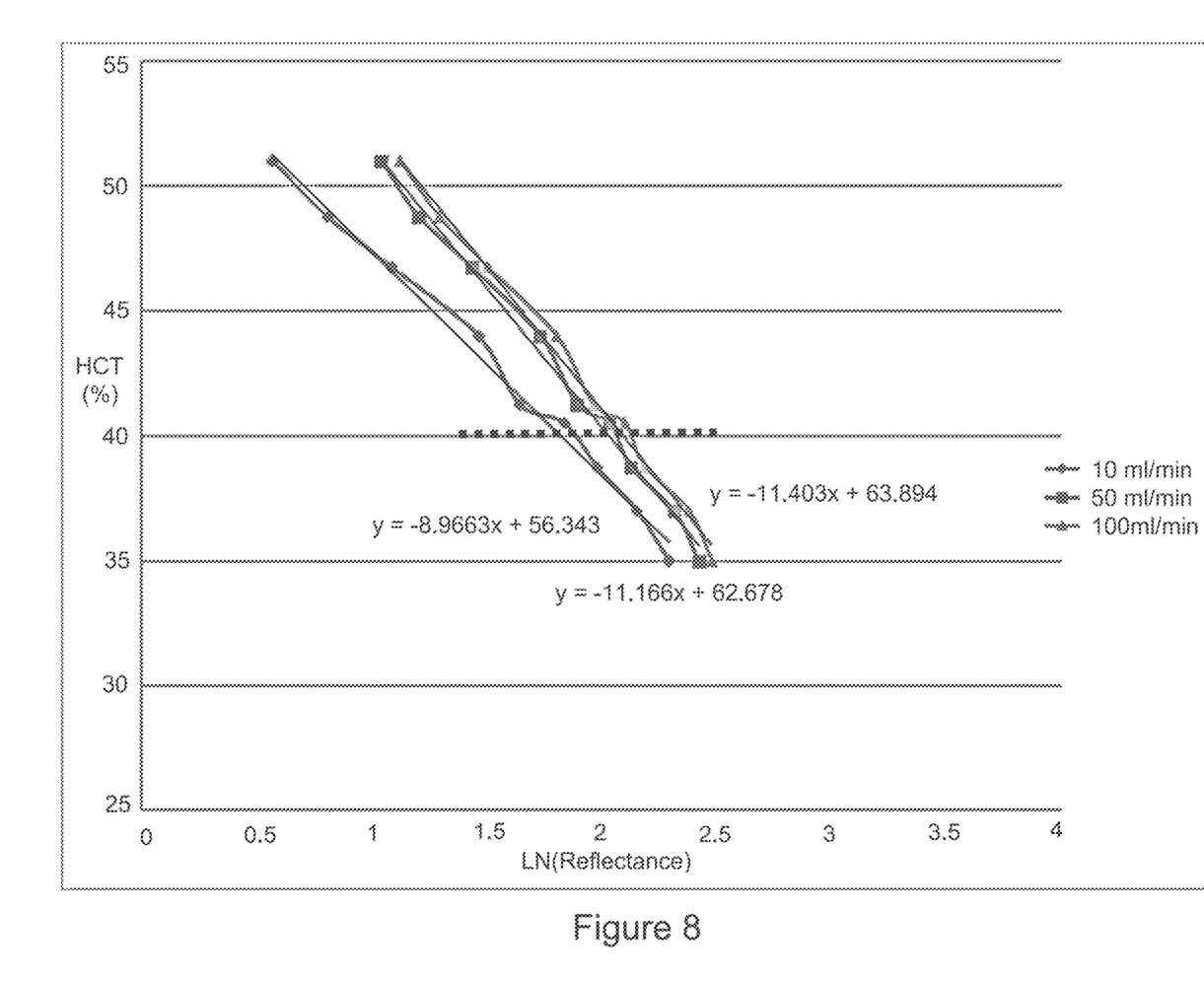
FIG. 8 is a graph of example correlation curves for infrared radiation (IR) reflection from WB, comparing hematocrit (HCT) to the natural log of reflection.

FIG. 8 displays example correlation curves for IR reflection (approx. 810 nm) from WB, comparing the HCT to the natural log of reflection (on the basis of Beer's law as explained in U.S. Pat. Nos. 9,164,078 and 6,419,822 and incorporated herein), for fluid flow rates of 10 ml/min, 50 ml/min, and 100 ml/min. The correlation curves represent experimental data which correlates the IR light reflected by blood to the HCT of the blood. If the HCT remains constant, such as 40% as indicated by the heavy horizontal dashed line in FIG. 8, then a new correlation curve comparing flow rates to light reflection may be formed and applied to measure the flow rate of the fluid in tubing 105', which again for convenience may represent tubing 105 in FIG. 6, and therefore, the description of the interaction of optical reflection sensor 104 and tubing 105' applies in the same manner for optical reflection sensor 104 and tubing 105 in FIG. 6.

Figure 9:
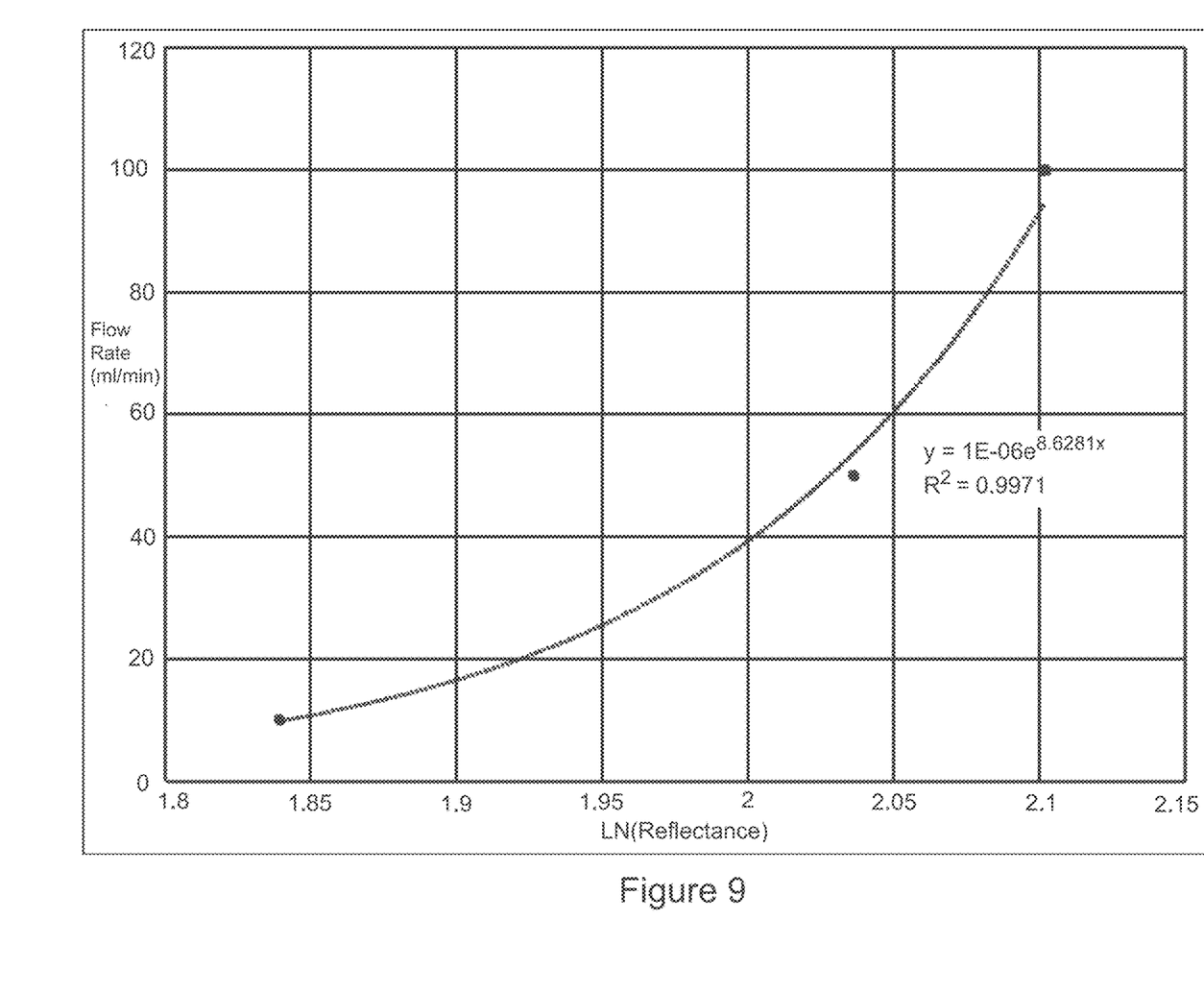
FIG. 9 is a graph of an example correlation curve comparing flow rates to the natural log of light reflection for 40% HCT WB flowing through a tubing.

FIG. 9 displays an example correlation curve comparing flow rates to the natural log of light reflection for 40% HCT WB flowing through tubing 105'. The correlation is an exponential relationship, which is expected because there is a maximum number of cells that may be congregated in the viewing area of the reflection sensor, and as flow rates increase, the cell concentration change in the center streamlines begins tapering off as open space is taken up by cell content. Therefore, depending on the diameter of the tubing and the sensor viewing area, the method may be limited to a specific flow rate range. For example, when using relatively small diameter tubing, flow rates greater than 100 ml/min may not create significant changes in light reflection. However, use of a large diameter tubing and a sensor having a larger viewing area may permit detection of significant changes in light reflection at flow rates greater than 100 ml/min.

A flow rate vs. LN (reflectance) correlation curve would be generated for every HCT in a desired range (ex: 35-55% for WB) and stored by the system (preprogrammed) for use based on the HCT value, which is the particulate value for the fluid that will be input by the user. Accordingly, correlation coefficients C1 and C2 will relate to respective correlation curves.

Figure 10:
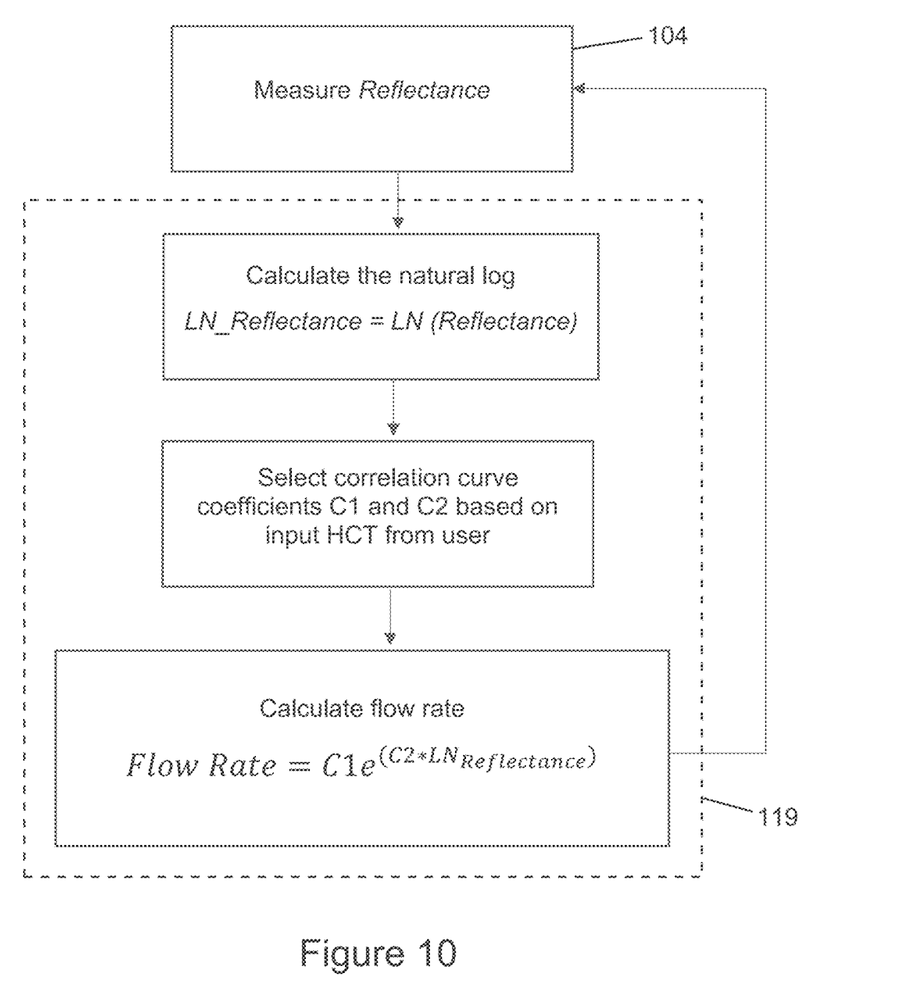
FIG. 10 is a flow chart of the logic for a sensor that measures Reflectance and interacts with a controller to measure fluid flow in accordance with the methods and systems disclosed herein.

FIG. 10 displays a flow chart of the method logic. There is a measurement of reflectance by the optical reflection sensor 104, which is communicated to the controller 119. Next, within the controller 119, among other processing functions, the controller calculates the natural log relating to the reflectance of particles in the fluid, where LN_Reflectance=LN (Reflectance). Then, there is a selection of correlation curve coefficients C1 and C2 based on the HCT value input by the user. Next, there is a calculation of the flow rate related to the two correlation curve coefficients and the natural log of the reflectance, where Flow Rate=$C1 e^{(C2*LN_{Reflectance})}$. It will be appreciated that to continue to measure and monitor the flow rate, the process may be repeated.

As noted previously, the device and method of using a non-invasive optical reflection sensor to measure flow rate of fluid flowing through a tubing may be utilized with other fluids having particles which result in reflectance. For example, with respect to the fluid processing system 110 shown in FIG. 6, an optical reflection sensor 120 may be used in a similar way to measure the fluid flow rate with respect to the packed RBCs that flow through tubing 114 to container 115.

According to an aspect of the present disclosure, a durable or reusable fluid separation system is used in combination with a separate fluid flow circuit (which may be disposable) to separate a plasma-containing fluid into separated plasma and a concentrated fluid. However, it will be appreciated that while FIG. 6 illustrates an exemplary fluid separation system 100, and FIG. 7 illustrates a portion of an exemplary fluid flow cassette that may be used in a fluid processing system, these are merely exemplary of such systems and circuits and that differently configured fluid processing systems and fluid flow circuits may be provided without departing from the scope of the present disclosure.

Similarly, while the system 100 of FIG. 6 is configured for processing WB, it may be used to process any other plasma-containing fluid to separate plasma from concentrated fluid (which may be red cell concentrate or packed red cells when the plasma-containing fluid constitutes whole blood), and is merely representative of a fluid processing system utilizing an optical reflection sensor to measure fluid flow rate.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

Other Aspects

Aspect 1. A method of optically measuring a fluid flow rate in a fluid processing system, comprising optically monitoring fluid flow through a transparent portion of a tubing by measuring light reflectance of particles in the fluid; calculating the natural log relating to the reflectance of particles in the fluid; selecting two correlation curve coefficients based on a particulate value for the fluid which is input by a user; and calculating a fluid flow rate related to the two correlation curve coefficients and the natural log of the reflectance.

Aspect 2. The method of Aspect 1 wherein optically monitoring further comprises utilizing a non-invasive sensor exterior to the tubing and that measures light reflectance for fluid flowing through the tubing.

Aspect 3. The method of Aspect 1 or 2 wherein optically monitoring further comprises using a sensor that is configured to transmit light and to detect reflected light.

Aspect 4. The method of Aspect 3 wherein the sensor is configured to transmit infrared light, light having one or more colors or Broadband light and to detect reflected light.

Aspect 5. The method of any of Aspects 1-4 wherein the calculated flow rate is equal to $C1e^{(C2*LN_{Reflectance})}$, wherein C1 and C2 represent the two selected correlation curve coefficients and $LN_{Reflectance}$ is the calculated natural log relating to reflectance of the particles in the fluid.

Aspect 6. The method of any of Aspects 1-5 wherein the fluid processing system further comprises an apheresis fluid separation system.

Aspect 7. The method of Aspect 6 wherein the particulate value further comprises a hematocrit value and the fluid further comprises blood.

Aspect 8. A method of measuring a flow rate of a fluid having particles, comprising providing a fluid flowing through a tubing; exposing the fluid in the tubing to a light emitted by a light source so as to cause at least a portion of the light to be reflected by the fluid; receiving at least a portion of the reflected light; analyzing at least a portion of the received light to determine a reflectance measurement of the at least a portion of the received light; correlating the reflectance measurement to a particulate value input by a user; and calculating a flow rate related to the reflectance measurement and the particulate value.

Aspect 9. The method of Aspect 8 wherein the light emitted by the light source is transmitted through a transparent surface of the tubing to be exposed to the fluid in the tubing, and the light emitted by the light source.

Aspect 10. The method of Aspect 8 or 9 wherein analyzing at least a portion of the received light further comprises calculating the natural log relating to the reflectance of particles in the fluid.

Aspect 11. The method of any of Aspects 8-10 wherein correlating the reflectance measurement to a particulate value further comprises selecting two correlation curve coefficients based on a hematocrit value input by the user.

Aspect 12. The method of Aspect 11 wherein calculating the flow rate further comprises calculating the flow rate related to the two correlation curve coefficients and the natural log of the reflectance measurement.

Aspect 13. The method of any of Aspects 8-12 wherein the tubing is part of an apheresis separation system and the particulate value further comprises a hematocrit value.

Aspect 14. The method of any of Aspects 8-13 wherein the light source is configured to emit infrared light or Broadband light including at least all wavelengths in the visible range.

Aspect 15. A device for measuring fluid flow rate using optical measurements and configured for use in combination with a tubing in a fluid processing system, comprising an optical sensor having a light source configured to emit a light, with at least a portion of the light being exposed to a fluid flowing through the tubing and being reflected; the optical sensor further comprising an optical fiber for receiving at least a portion of the reflected light; and a controller configured to correlate the received reflected light relative to two correlation curve coefficients based on a particulate value input by a user and to calculate an output indicative of the flow rate of the fluid flowing through the tubing.

Aspect 16. The device of Aspect 15 wherein the optical sensor further comprises a non-invasive optical sensor exterior to the tubing.

Aspect 17. The device of any of the Aspects 15-16 wherein the optical sensor is configured to transmit infrared light or Broadband light and to detect reflected light.

Aspect 18. The device of any of the Aspects 15-17 wherein the calculated output for the flow rate is equal to $C1e^{(C2*LN_{Reflectance})}$, wherein C1 and C2 represent the two selected correlation curve coefficients and $LN_{Reflectance}$ is the calculated natural log relating to reflectance of the particles in the fluid.

Aspect 19. The device of any of the Aspects 15-18 wherein the fluid processing system further comprises an apheresis separation system.

Aspect 20. The device of any of the Aspects 15-19 wherein the particulate value further comprises a hematocrit value.

Aspect 21. The device of any of the Aspects 15-20 wherein the light source is configured to emit infrared light or Broadband light including at least all wavelengths in the visible range.

Aspect 22. A method of measuring a flow rate of a fluid, comprising providing a fluid flowing through a tubing; exposing the fluid in the tubing to a light emitted by a light source so as to cause at least a portion of the light to be reflected by the fluid; receiving at least a portion of the reflected light; analyzing at least a portion of the received reflected light to determine a reflectance measurement; correlating the reflectance measurement to a particulate concentration; and generating an output indicative of the flow rate corresponding to the reflectance measurement.

Aspect 23. The method of Aspect 22 wherein the particulate concentration is based on an inputted hematocrit level.

Aspect 24. The method of any of Aspects 22-23 wherein the light emitted by the light source is infrared light or Broadband light that is transmitted through a transparent surface of the tubing to be exposed to the fluid in the tubing, and the reflectance of the light emitted by the light source is measured.

Aspect 25. The method of any of Aspect 22-24 wherein correlating the reflectance measurement to a particulate concentration further comprises selecting two correlation curve coefficients based on a hematocrit value input by the user.

Aspect 26. The method of Aspect 25 wherein generating the output indicative of the flow rate corresponding to the reflectance measurement further comprises calculating the flow rate related to the two correlation curve coefficients and the natural log of the reflectance measurement.

Aspect 27. An optical sensor device configured for use in combination with a fluid flowing through a tubing, the optical sensor device comprising a light source configured to emit a light, with at least a portion of the light being exposed to a fluid in the tubing and reflected; an optical sensor configured to receive at least a portion of the reflected light and analyze at least a portion of the received reflected light to determine a reflectance measurement; and a controller configured to correlate the reflectance measurement to an input particulate level and generate an output indicative of the fluid flow rate corresponding to the reflectance measurement.

Aspect 28. The device of Aspect 27 wherein the particulate concentration is based on an inputted hematocrit level.

Aspect 29. The device of any of Aspects 27-28 wherein the light source is configured to emit infrared light or Broadband light including at least all wavelengths in the visible range.

Aspect 30. The device of any of Aspects 27-29 wherein the light emitted by the light source is transmitted through a transparent surface of the tubing to be exposed to the fluid in the tubing, and the reflectance of the light emitted is measured.

Aspect 31. The device of any of Aspects 27-30 wherein correlation of the reflectance measurement to a particulate concentration further comprises selection of two correlation curve coefficients based on a hematocrit value input by the user.

Aspect 32. The device of Aspect 31 wherein generating the output indicative of the flow rate corresponding to the reflectance measurement further comprises calculating the flow rate related to the two correlation curve coefficients and the natural log of the reflectance measurement.

Aspect 33. In a blood processing procedure in which blood is processed into one or more blood components with a single-use processing kit, the processing kit including tubing through which the blood is flowed, and a reusable hardware module onto which the processing kit is mounted, the reusable hardware module including a sensing field defined by a segment of the tubing to which a non-invasive optical reflection sensor is directed, a method for measuring the fluid flow rate of the blood comprising loading the processing kit onto the hardware module with a segment of the tubing positioned in the sensing field; flowing blood through the segment of the tubing; accepting input of a hematocrit level of the blood flowing through the segment of the tubing positioned in the sensing field; utilizing the optical reflection sensor to apply light to the blood flowing through the tubing in the sensing field and obtain a reflectance measurement of the segment of the tubing through which said blood is flowing; deriving the natural log of the infrared reflectance measurement attributable to the blood flowing in the segment of the tubing; selecting correlation curve coefficients based on the input hematocrit level; utilizing the natural log of the reflectance attributable to the blood in the segment of the tubing and the correlation curve coefficients in a correlation equation to arrive at the fluid flow rate measurement of the blood flowing through the tubing in the sensing field; and outputting the fluid flow rate measurement of the blood.

Aspect 34. The method of Aspect 33 wherein the blood comprises whole blood.

Aspect 35. The method of Aspect 33 wherein the blood comprises concentrated red blood cells.

Aspect 36. The method of Aspect 33 wherein the blood comprises a blood product including red blood cells.

The invention claimed is:

1. A method of optically measuring a fluid flow rate in a fluid processing system, comprising:
   optically monitoring fluid flow through a transparent portion of a tubing by measuring light reflectance of particles in the fluid;
   calculating the natural log relating to the reflectance of particles in the fluid;
   selecting two correlation curve coefficients based on a particulate value for the fluid which is input by a user; and
   calculating a fluid flow rate related to the two correlation curve coefficients and the natural log of the reflectance.

2. The method of claim 1 wherein optically monitoring further comprises utilizing a non-invasive sensor exterior to the tubing and that measures light reflectance for fluid flowing through the tubing.

3. The method of claim 2 wherein optically monitoring further comprises using a sensor that is configured to transmit light and to detect reflected light.

4. The method of claim 3 wherein the sensor is configured to transmit infrared light, light having one or more colors or Broadband light and to detect reflected light.

5. The method of claim 1 wherein the calculated flow rate is equal to $C1e^{(C2*LN_{Reflectance})}$, wherein C1 and C2 represent the two selected correlation curve coefficients and $LN_{Reflectance}$ is the calculated natural log relating to reflectance of the particles in the fluid.

6. The method of claim 1 wherein the fluid processing system further comprises an apheresis fluid separation system.

7. The method of claim 6 wherein the particulate value further comprises a hematocrit value and the fluid further comprises blood.

8. A device for measuring fluid flow rate using optical measurements and configured for use in combination with a tubing in a fluid processing system, comprising:

an optical sensor having a light source configured to emit a light, with at least a portion of the light being exposed to a fluid flowing through the tubing and being reflected;

the optical sensor further comprising an optical fiber for receiving at least a portion of the reflected light; and a controller configured to correlate the received reflected light relative to two correlation curve coefficients based on a particulate value input by a user and to calculate an output indicative of the flow rate of the fluid flowing through the tubing.

9. The device of claim 8 wherein the optical sensor further comprises a non-invasive optical sensor exterior to the tubing.

10. The device of claim 8 wherein the optical sensor is configured to transmit infrared light or Broadband light and to detect reflected light.

11. The device of claim 8 wherein the calculated output for the flow rate is equal to $C1e^{(C2*LN_{Reflectance})}$, wherein $C1$ and $C2$ represent the two selected correlation curve coefficients and $LN_{Reflectance}$ is the calculated natural log relating to reflectance of the particles in the fluid.

12. The device of claim 8 wherein the fluid processing system further comprises an apheresis separation system.

13. The device of claim 8 wherein the particulate value further comprises a hematocrit value.

14. The device of claim 8 wherein the light source is configured to emit infrared light or Broadband light including at least all wavelengths in the visible range.

15. A method of measuring a flow rate of a fluid, comprising:

providing a fluid flowing through a tubing;

exposing the fluid in the tubing to a light emitted by a light source so as to cause at least a portion of the light to be reflected by the fluid;

receiving at least a portion of the reflected light;

analyzing at least a portion of the received reflected light to determine a reflectance measurement;

correlating the reflectance measurement to a particulate concentration; and generating an output indicative of the flow rate derived from the reflectance measurement, and wherein correlating the reflectance measurement to a particulate concentration further comprises selecting two correlation curve coefficients based on a hematocrit value input by the user.

16. The method of claim 15 wherein the particulate concentration is based on an inputted hematocrit level.

17. The method of claim 15 wherein the light emitted by the light source is infrared light or Broadband light that is transmitted through a transparent surface of the tubing to be exposed to the fluid in the tubing, and the reflectance of the light emitted by the light source is measured.

18. The method of claim 15 wherein generating the output indicative of the flow rate derived from the reflectance measurement further comprises calculating the flow rate related to the two correlation curve coefficients and the natural log of the reflectance measurement.

19. A device for measuring a flow rate of a fluid through a tubing, comprising:

a tubing configured to receive a fluid flow;

a light source oriented to emit light toward the tubing;

an optical sensor that receives at least a portion of light reflected by fluid flowing through the tubing;

a controller in communication with the optical sensor and configured to analyze at least a portion of the received reflected light to determine a reflectance measurement and to correlate the reflectance measurement to a particulate concentration and generate an output indicative of the flow rate derived from the reflectance measurement.

20. A device for measuring fluid flow rate and configured for use in combination with a tubing in a fluid processing system, comprising:

a light source that emits light, with at least a portion of the light being exposed to a fluid flowing through the tubing and being reflected by the fluid;

an optical sensor comprising an optical fiber for receiving at least a portion of the reflected light; and a controller configured to analyze at least a portion of the received reflected light to determine a reflectance measurement and to correlate the reflectance measurement to a particulate concentration and generate an output indicative of the flow rate derived from the reflectance measurement.

* * * * *